United States Patent [19]

Cox, Jr. et al.

[11] Patent Number: 5,032,727
[45] Date of Patent: Jul. 16, 1991

[54] PRODUCT DEFECT DETECTION USING THERMAL RATIO ANALYSIS

[75] Inventors: Eldon E. Cox, Jr., Lowell; Michael P. Rolla, Maynard, both of Mass.

[73] Assignee: Digital Equipment Corporation, Maynard, Mass.

[21] Appl. No.: 582,102

[22] Filed: Sep. 14, 1990

[51] Int. Cl.⁵ .......................................... H01L 31/00
[52] U.S. Cl. .................................. 250/330; 250/332; 358/106; 374/4; 374/5; 382/1; 382/43
[58] Field of Search ............ 356/237, 389, 391, 394, 356/445; 358/106, 113; 374/4, 5, 10, 45, 57; 250/330, 332, 341, 342; 382/1, 34

[56] References Cited

U.S. PATENT DOCUMENTS

| | | | |
|---|---|---|---|
| 4,061,578 | 12/1977 | Kleinerman | 250/330 |
| 4,154,085 | 5/1979 | Hentze | 374/10 |
| 4,513,441 | 4/1985 | Henshaw | 356/257 |
| 4,558,222 | 12/1985 | Neil | 250/330 |
| 4,755,874 | 7/1988 | Esrig et al. | 358/101 |
| 4,759,072 | 7/1988 | Yamane et al. | 250/330 |
| 4,816,681 | 3/1989 | Shimura | 250/327.2 G |
| 4,872,052 | 10/1989 | Lindzius | 358/106 |

OTHER PUBLICATIONS

C. G. Masi, "What Can Thermal Imaging do for You?", Test and Measurement World, May, 1988.
C. G. Masi, "Finding Board Faults with Thermal Imaging", Test and Measurement World, Mar., 1989, pp. 100, 111 and 112.
"Thermal Imager Product Survey", Test and Measurement World, Mar., 1989, pp. 113-115, 120.
Hugh Danaher, "Thermography-Understanding the Expanded Role of Thermal Imagers in Production Testing", Evaluation Engineering, Dec., 1988, pp. 74, 75, 77-79.

Primary Examiner—William A. Cuchlinski, Jr.
Assistant Examiner—G. Bradley Bennett
Attorney, Agent, or Firm—Finnegan, Henderson, Farabow, Garrett and Dunner

[57] ABSTRACT

A method and apparatus for indicating defects in manufactured products employs, instead of the conventional thermal image subtraction, "thermal ratio analysis", which involves ratios of thermal data and their analysis including statistical analysis. Various techniques for "image" enhancement and for suppression of known artifacts are employed to facilitate the decision as to when a defect is detected. The thermal ratio analysis technique is particularly useful for detecting hidden defects in electronic circuitry, such as integrated circuits.

40 Claims, 7 Drawing Sheets

PRODUCT DEFECT DETECTION USING THERMAL RATIO ANALYSIS

FIELD OF THE INVENTION

The present invention relates to product defect detection using thermal analysis.

BACKGROUND OF THE INVENTION

The early discovery of hidden defects in parts and products is of increasing concern to manufacturers as they strive to obtain superior product quality. Particularly, there is a need for the early discovery of defects which could remain latent, or undiscovered, for an indeterminate time.

Thermography, or thermal analysis, has attracted considerable recent attention as one way of discovering such defects. All objects "glow" from thermal radiation with an intensity and "color" which is dependent upon the temperature. At room temperature this "color" is within a range known as infrared and cannot be seen with the unaided eye. At extreme temperatures an object will glow visibly as in the case of iron heated in a fire. This property can be used to measure the temperature of a surface without need for any kind of contact. Any of several types of equipment can convert this temperature information into a black and white or color image that represents the temperatures within the scene. Such equipment can be called a "thermal imager" and can be used to study non-visible properties of electronic assemblies in the hope of locating defective devices.

It has long been known that patterns of heating effects (e.g., patterns of the infrared glow) in a product may be affected by a latent defect; but the heating effect may not be readily detectable for some types of defects. Particularly in bipolar semiconductor circuits, prior thermal analysis ("thermography") techniques have been only marginally effective in locating defects, except in certain limited situations.

Frequently, the analysis techniques employed with such equipment involve elevating the temperature of the object for at least one of several images. Then images obtained under different conditions are compared in an attempt to remove everything from the image which is normal and leave only the image features that relate to the defect. In the case of semiconductor circuits or components, the different conditions can be the normal powered state and normal non-powered state.

One of these prior analysis techniques is known as image subtraction. Generally, in this technique an image, comprising a regular array of values representing infrared radiation, is obtained from a reference sample, which is a high-quality sample of the product, and is subsequently subtracted from a similar image obtained from a test sample, which is a sample, of unknown quality, of the product. The purpose is to remove features from the difference image which are known to be normal, so as to increase the likelihood that any residue in the difference image is indicative of a defect in the product. Available thermal analysis techniques use image subtraction in one form or another. For example, see the description in the article by C. G. Masi, "Finding Board Faults With Thermal Imaging", *TEST AND MEASUREMENT WORLD*, March., 1989 pp. 100, 111, 112. The image subtraction technique in this article, as described in connection with a circuit board, starts with the board in a known thermal state (e.g., the entire board at 22° C.). The test operators then apply a given power source to the board and monitor changes in the thermogram as the board heats up to operating temperature.

The basic phenomenon employed in image subtraction thermography for such products is black-body radiation from ohmic heating of current-carrying traces and components, as explained in the article by C. G. Masi, "What Can Thermal Imaging Do For You?" *TEST AND MEASUREMENT WORLD*, May, 1988. It is also known, however, that image subtraction thermography can be applied to non-current-carrying products, to the extent such products can be subjected to controlled thermal changes.

The monitoring of thermal changes by image subtraction is based on the premise that the thermal changes for a non-defective product should be different from the thermal changes for a defective product. Thus, if the thermogram for a known non-defective product (sample) is subtracted from the thermogram for a product ( or sample) being tested, the differences, if any, are hoped to be indicative of a defect. Conversely, if a hidden defect does exist in a sample, it is hoped that it will produce a thermogram which is different from the thermogram of the non-defective sample. The greatest successes in the prior art techniques have been for products which produce relatively little heat. However, products such as transistor-transistor-logic circuits which produce much heat have yielded marginal success in diagnostic testing using prior art techniques. The problem appears to be that the variability of heating among non-defective (normal) samples can be much larger than the effect upon heating produced by a sample having a subtle defect. This tendency makes such defect difficult, if not impossible, to detect by previously known image subtraction techniques.

SUMMARY OF THE INVENTION

It is an object of the present invention to overcome the limitations of image subtraction thermography. It is desirable to provide a method and apparatus to emphasize those thermographic differences between a reference sample and a test sample which are likely to be indicative of a defect, relative to differences which are not likely to be related to a defect.

Additional objects and advantages of the invention will be set forth in part in the description which follows and in part will be obvious from the description, or may be learned by practice of the invention. The objects and advantages of the invention may be realized and obtained by means of the instrumentalities and combinations particularly pointed out in the appended claims.

The invention is based upon the recognition that more defect-sensitive analysis can be achieved by obtaining a ratio of variables related to thermographic responses to two differing non-equilibrium thermal stimuli, applied first to a previously tested product ("reference sample"), known to be good, and then applied subsequently to a test sample of the same product. The term "thermal stimulus" or "thermal stimuli" as used herein refers to any stimulus, not necessarily thermal in origin, which when applied to a sample of a product, ultimately has an effect of changing the temperature thereof. A stable base level, or equilibrium, thermogram for each sample also is involved in determining the variables.

Four difference records relating to the reference sample and the test sample are generated, and therefrom at least one ratio record is derived. A composite record is formed from the ratio record and the unused difference records; and a defect indication is generated when the composite record yields a statistically significant deviation from an expected value.

The statistical basis for such defect detection will be discussed in detail later.

The technique of this invention has been termed Thermal Ratio Analysis (TRA). The invention resides both in a method and in test equipment for obtaining at least one pattern of thermal ratios from a plurality of thermal difference records obtained from a reference sample and from a test sample, and for forming a composite record including at least one pattern of thermal ratios. Since these samples are like samples of the same part or product, they will be termed a "reference sample" and a "test sample".

According to a principal feature of the invention, a method of detecting a defect in a test sample of a manufactured device is provided which comprises the steps of: establishing a reference record for at least one reference sample of the device, comprising the sub-steps of:

(1) making a base thermal record of the reference sample at a base value of a thermal stimulus;

(2) making a plurality of changed value thermal records of the reference sample at a plurality of respective changed values, compared to the base value, of the thermal stimulus, including applying a respective changed-value thermal stimulus to the sample; and (3) making a first difference record from the base-value thermal records and one of the plurality of changed value thermal records and a second difference record involving at least another of the plurality of changed-value thermal records, the first and second difference records each comprising a plurality of data points in an image-related array;

generating a test record for the test sample by repeating sub-steps (1)-(3) with the test sample replacing the reference sample;

deriving at least one ratio record from the four difference records consisting of the first and second difference records for the test sample and the first and second difference records for the reference sample;

forming a composite record including at least the derived one ratio record; and generating a defect indication when the composite record yields a statistically significant deviation from an expected value.

In the preferred embodiment, the thermal stimuli which are changed in the steps of producing first and second thermographs are voltages of first and second magnitudes that are applied to the samples in such a way as to produce heating therein; and the base-level thermograph is an ambient-temperature thermograph.

One embodiment is immediately applicable to electronic components on a populated circuit board and can be extended by use of masking and filtering techniques, sometimes called image enhancement techniques, and by use of robotic scanning control, to integrated semiconductive circuits, in particular, packaged ones, mounted on ceramic substrates or printed circuit boards.

In another embodiment of the invention, the thermal stimuli are voltages which are changed in duration rather than magnitude. This embodiment is advantageous, among other reasons, if electronic components or circuitry such as semiconductor components or circuitry are to be tested under conditions more realistic as related to an intended mode of operation in a computer or a timing program control. In fact, it is certainly reasonable to consider doing some carefully-timed operational testing simultaneously with the thermal ratio analysis.

The principles of the invention extend to all products that can be thermographically tested. For non-current-carrying products, microwave radiation can be considered as one likely stimulus to be employed. In such manner, these products or, more specifically, test samples of these products, can be tested by methods and equipment within the scope of the appended claims.

The accompanying drawings, which are incorporated in and constitute a part of this specification, illustrate one preferred embodiment of the invention and, together with the description, serve to explain the principles of the invention.

DESCRIPTION OF THE PREFERRED EMBODIMENTS

Figure 1:
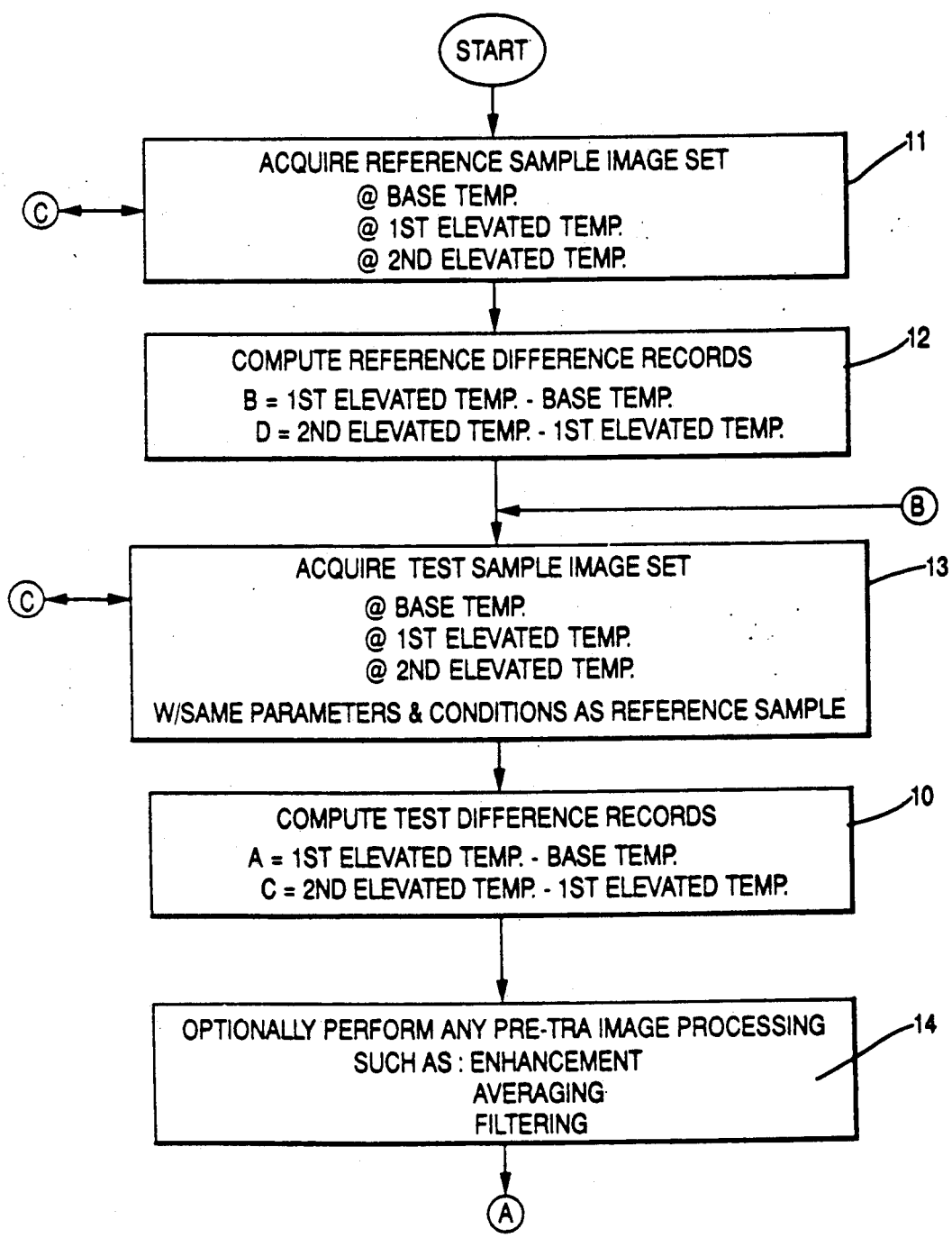
FIGS. 1-5 are flow diagrams illustrating steps of the method of the invention.

An example of the preferred method is shown in the flow diagrams of FIGS. 1-5.

The method of the invention overcomes the limitations of image subtraction techniques by compensating for the expected thermal variations among like samples of a given product. The invention works on the premise that the ratio of heating of like samples under different thermal stimuli should be a constant. If a functional defect or other abnormality is present in a sample, it is expected to cause the thermal response for at least one of the thermal stimuli to deviate from the expected value; and this expectation has been borne out in practice. This alters the ratio of heating observed for that sample at a particular data point in an image-related array of data points and thus indicates that data point as the locus of either an actual defect, a defect-related symptom, or a latent defect. For purposes of this application, a defect is any deviation from acceptable quality or properties of a product.

Normal thermal variations cancel when ratios of two arrays of image differences are derived for measurements from the same sample or from the reference sample and the test sample. To complete the technique, the measurements are formed into a composite record including two other arrays of image differences, for corresponding data points in each array, for the reference sample and the test sample. Illustratively, to form a composite set of measurements, a different ratio record can be derived, and then the ratio of the ratio records can be taken as a means of discerning correct from incorrect temperature profiles. In general, a defect is indicated when an anomalous region or datum appears in the composite record.

At present two types of stimuli have been identified as being useful with TRA in accordance with the present invention. The first and simplest is to vary the voltage applied to power the sample - typically using the maximum and minimum voltages specified for the sample. The sample can be a stand-alone sample or part of a larger functional group. It can be tested in a totally static test, or in a full simulation of its expected operation, if timing constraints of the thermal ratio analysis are compatible therewith. Static testing does, however, eliminate the possible interaction of a simulation and heating effects, that is, operation altered by software taking non-normal decision-loop branches during the simulation due to the defect. The simulation type of test purposely depends upon the heating effects introduced by two software routines or clocked verses non-clocked operation -- in fact, this type of test simply can be designed to simulate operation of the sample and even to simulate the effect of the more unusual durational stresses of signals upon the sample, by primarily affecting the duration of each stimulus instead of its magnitude.

The thermal variation observed between different non-defective samples of a product is largely due to manufacturing and design tolerance within the samples themselves. For electronic circuitry, this variation has both a linear and non-linear ohmic component with respect to the applied voltage and is also subject to any dynamic stimulation applied. The amount of temperature rise above ambient is related linearly to the power dissipated multiplied by some constant, in the case of an integrated circuit, due to the packaging thereof. This packaging can vary from circuit to circuit but is not a function of any external stimuli. Thus, the temperature rise expected to be observed is, internally, a function of the packaging and the linear and non-linear resistances and, externally, a function of the applied voltage and dynamic stimulation (i.e., software).

Defects can manifest themselves as modifications of the internal resistive structures of an electronic sample and are difficult to discern from normal variations using standard image subtraction. It is not understood from prior art thermography techniques that taking the ratio between two temperature rises will produce a characteristic thermal signature of a product, or a point in a product. Defects also have a strong tendency to be functions of the external variables which differ from those functions exhibited by their normal counterparts. For example, the non-linear resistances of normal samples of a product usually have the same non-linear relationship and differ only by a linear constant. If a sample is stimulated by applying power at two different voltages, and the subsequent steps of our invention are employed, the two measured temperatures at any corresponding data points will be related by two terms: (1) the non-linear resistance expressed as a function of the ratio of the applied voltages (the ratio raised to the power $\alpha$, where $\alpha$ does not equal 0), and (2) the square of the ratios of the two voltages. All the linear relationships which are equally shared will drop out.

Thus the ratio of temperature rise above ambient for two different voltage levels should be a constant from sample to sample of the same product. Even the thermal constant of the package drops out of the calculation except in cases of extreme changes in packaging. It is therefore possible to measure a reference sample and a test sample of the same product and substantially to cancel or eliminate the expected variation, by following analysis steps appropriately including at least one ratio, and, illustratively, steps including taking a ratio of ratios. When this is done, as it will be mathematically shown below, then all of certain terms in the expression for the values of the image-related data points, even the term related to the square of the voltages, drop out.

What is left is an image highlighting only those pixels (data points in the resulting array) for which the reference sample and the test sample exhibit substantial differences in their "non-linear" characteristics.

A mathematical derivation of the principles just described concerning the use of a dual-level voltage stimulus for thermal ratio analysis, in accordance with the invention, follows:

The temperature rise $\Delta T$ above the ambient of a sample is equivalent to the power dissipation (Pd) multiplied by a constant (Cp) related to the packaging and heat-sinking of the sample.

$$\Delta T = T(E) - T_{ambient} = Cp \times Pd(E),$$

where T(E) is the elevated temperature produced by applied voltage E.

$$\text{Since: } P = E \times I(E) \quad (1)$$

$$\Delta T = Cp \times E \times I(E) \quad (2)$$

Since:

$$I(E) = E/R(E) \quad (3)$$

$$\Delta T = Cp \times E^2/R(E) \quad (4)$$

But resistance can be replaced by its reciprocal G, conductance:

$$\Delta T = Cp \times E^2 \times G(E) \quad (5)$$

Conductance can be modeled as a function of E with linear and non-linear terms . . .

$$G(E) = \beta \times E^\alpha \quad (6)$$

$$\Delta T = Cp \times E^2 \times \beta \times E^\alpha, \quad (7)$$

the relationship being non-linear to a degree dependent upon the degree to which $\alpha$ deviates from zero. If images are taken at two voltage levels and the temperature difference ratio, $T_{2:1}$ taken between them, then . . .

$$T_{2:1} = (\Delta T_2/\Delta T_1) = (Cp \times E_2^2 \times \beta \times E_2^\alpha)/(Cp \times E_1^2 \times \beta \times E_1^\alpha) \quad (8)$$

$$T_{2:1} = \frac{E_2^2}{E_1} \times \frac{E_2^\alpha}{E_1} \quad (9)$$

At this point, many of the unwanted terms have already cancelled out.

Assume a reference sample is imaged and has a temperature ratio of $T_{rs}$ and a test sample has a ratio of $T_{ts}$. Taking the ratio of the ratios yields. . .

$$\frac{T_{ts\,2:1}}{T_{rs\,2:1}} = \frac{E_2}{E_1} (\alpha_{ts} - \alpha_{rs}) \quad (10)$$

Thus the resultant image is a function only of the applied voltages and the difference in the non-linear component of the internal resistances. That is, detectable differences exist at the array of data points when $\alpha_{ts}$ does not equal $\alpha_{rs}$, which in general will be true when the $\alpha$'s do not equal 0. If the non-linear resistances are equal, then the result goes to unity. Thus, this can become a sensitive measure of non-linear defects, because the small, but readily variable, non-linear term is not swamped by larger linear variations, which have cancelled out.

It is also possible to hold the voltage constant and to vary the dynamic stimuli, usually by changing the software or by turning a clock on or off. The mechanism used here is that the heat generated by a defect will depend upon how the duration of a thermal stimulus is changed as well as upon its magnitude.

Figure 7:
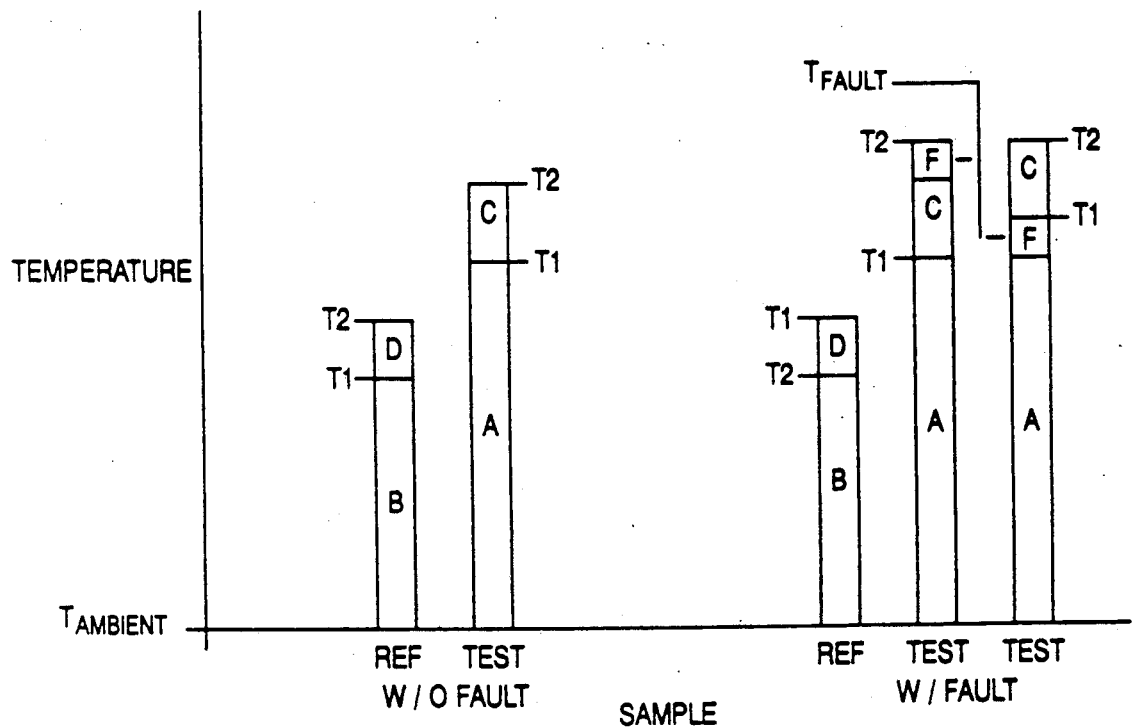
FIG. 7 is a bar graph showing temperature relationships for comparable points for a reference sample and a test sample.

The general temperature relationships for any TRA, regardless of stimulus, can be seen in the diagram in FIG. 7.

The temperatures measured in response to the two stimuli are T1 and T2. The original ambient temperature is Ta.

In the case of two non-defective samples of the same product, the ratio of temperatures due to the two stimuli should be equal between the reference sample and the test sample, within the limits of noise and measurement error. From the mathematical development above and by reference to FIG. 7, we have:

$$\frac{A/B}{C/D} = 1 \tag{11}$$

$$\frac{A}{B} = \frac{C}{D} \text{ or } \frac{A}{C} = \frac{B}{D} \tag{12}$$

These are obtained directly by measuring Ta, T1, and T2 for both samples and performing the appropriate subtractions. (For example, D=T2-T1 for the reference sample).

In the case of a defective sample, the original temperature components (A, B, C and D) can be considered to be identical to the scenario relating to non-defective samples. However, they are not directly measurable due to the temperature component added by the defect (F) - see FIG. 7. As shown, the defect temperature component F could show up as a function of either or both thermal stimuli.

Without carrying the analysis further, one can then arrange thermal ratio analysis to involve the use of three ratios, first, following either of the alternative forms of equation (12) to obtain two of the ratios, and then taking a ratio of ratios for each data point as suggested by equation (11).

In practical terms, once one has the four difference records generated as described above, TRA can be carried out fundamentally by the following: deriving first and second ratio records from the first and second difference records for the reference sample and the first and second difference records for the test sample, either by taking the ratio of the first difference records and the ratio for the second difference records in the same order, after which one takes the ratio of the ratios, or by taking the ratio for the difference records for the reference sample and the ratio for the difference records for the test sample in the same order, after which one takes the ratio of the ratios.

An estimate of F can be made by assuming that F only modifies the value of C. (Other approximating assumptions can also be made to like effect). By rearranging the equation above, an estimate of what C should be, based on the measured values of A, B and D, can be made. This is then subtracted from the value (C') measured for T2-T1 for the test sample.

$$C = D \times \frac{A}{B} \tag{13}$$

$$C' = C + F \tag{14}$$

$$F = C' - C = C' - D \times \frac{A}{B} \tag{15}$$

Equation (15) is just one of many approximate algebraic transformations of equation (11).

In fact, as equation (15) suggests, in this algebraic transformation of equation (11), TRA can be considered to be a particular type of image subtraction which has been normalized to compensate for predictable variations between like components. This is a particularly useful embodiment of the invention.

Looked at another way, this approximate form of TRA requires, in its simplest form, that only one ratio be taken, the ratio being taken for comparable difference records from the reference sample on the one hand, and the test sample on the other hand, providing one is willing to accomplish the multiplication and ultimate or "normalized" difference taking, involving the other difference records.

The preceding analysis demonstrates the simplicity of TRA, showing why it provides an image in which many otherwise expectable artifacts are removed because of the use of ratios.

From equations (10) and (11) it is established that a ratio of ratios calculated from the measured thermal values should equal one (1) in cases where no defect exists. If desired, it is also possible to present the thermal ratio relationship in an alternate form by means of any applicable algebraic transformation. Equation (15) is an example of a transformation that affects the thermal information such that values corresponding to no defect tend toward zero (0) instead of one. This form also has the advantage that calculated values will be symmetrical on either side of the no defect level.

In either case, there is some natural variation, or scatter, in all measurements that will follow statistical laws. For this reason the results of a TRA calculation will never exactly go to one for equation (11) [or zero for equation (15)]. Instead there will be random distribution of data values, or scatter, which will be centered around the central value. This distribution will be strongly center weighted and will have some characteristic spread (i.e., standard deviation) that is dependent on environmental factors and the quality of the components in the TRA system. Presented as an image, this would appear as some degree of noise or non-uniformity in an otherwise uniform background.

The TRA values associated with defects will tend to not approach the central value (one or zero, depending on the equation used). The method for the detection of defect-related thermal information is a simple statistical test. A value for the spread, or scatter, of the measurement data is calculated (standard deviation is a good measure). This spread may encompass the entire test field, or only a local area of it. A threshold is set based upon a multiple of this spread value. Common statistical practice usually picks a multiple between two and three times the standard deviation ("sigma"). This threshold is then set above and below the central value. If a multiple of two is used, then 95% of the normal noise should fall between the two thresholds. If the multiple is three, then 99% of the normal noise should fall between the limits. Any TRA value that falls beyond one of these ranges represents a possible indication of a fault.

The certainty of the defect indication can be biased by two considerations. First, values that far exceed the thresholds usually can be considered to be stronger defect indications than form an image, most real components are large enough that at least several distinctive adjacent thermal ratio analysis values will correspond to a given component. The uncertainty of the defect indication is inversely proportional to the number of related TRA image values that exceed the thresholds. Thus, a general principle is that the more image points that correspond to a component, where these image points have substantial contrast with respect to the general background, the lower the threshold can be to maintain a given certainty for the defect. For any given size of component (in terms of number of image values) it is possible to set a dynamic test threshold that maintains a fixed probability of falsely indicating a good device or not detecting a defective device. These are standard statistical methods for detecting desired features in the presence of noise.

The emphasis on defect detection up to this point has been in regard t the preferred embodiment of the invention in which the TRA data values comprise an image. In that case, the formal statistical approach to defect detection presented above can often be abandoned in favor of a more intuitive approach based on visual inspection of the image. Simply stated, defects will appear as points or regions which stand out by virtue of a significant (or greater than average) contrast in displayed intensity (or color) from the rest of the image.

The invention however is not restricted to imaging applications alone. An embodiment of the invention is possible in which discrete temperature measurements are made only at single points, usually corresponding to individual components on a unit. Obviously such measurements are not spatially related to each other and do not form an image array of data values. In this case the formal statistical analysis is required to discern defect-related thermal values from normal ones. However, much less data is available to establish a reference threshold because the non-component areas of the unit are not available for examination. The statistical method described above is still valid, however, due to the fact that in a real manufacturing environment most components will indeed be good (non-defective) and the data values of the good components correspondingly will reflect this. Thus the data values of the good components will provide sufficient statistical information to enable the detection of defective component(s). The ability to detect thermally subtle defects will not be as accurate as the imaging version of this invention due to the smaller amount of information available for processing. As in all cases of statistical testing, accuracy is directly related to the amount of data available.

ERROR FACTORS

Some explanation needs to be given to the factors that contribute to the introduction of error into the TRA image. The amount of quantization error prior to any image pre-processing can be estimated from the form of the approximate TRA formula:

$$F = C - D \times \frac{A + \epsilon}{B + \epsilon} \tag{16}$$

Before this can be used however, the variables that introduce error should first be considered. The uncertainty ($\partial T$) in any temperature measurement T is equivalent to the minimum temperature resolution of the imager Tr (usually $+/-0.05$ degree C.), plus any uncertainty due to taking the image prior to thermal stabilization. This will be called the temperature stabilization error, Tse, so that:

$$\partial T = Tr + Tse \tag{17}$$

To estimate Tse, the temperature stabilization function must be modeled. This can be considered to roughly approximate an exponential which has an associated time-constant, and that ultimately reaches some upper temperature limit, Tmax. Expressed as a function of the time (t) and the time-constant ($\tau$), the temperature stabilization function is:

$$Ts(\tau,t) = Tmax \times (1 - e^{-t/\tau}) \tag{18}$$

To express the uncertainty of Ts in terms of the values and uncertainty of $\tau$, and t, we can use:

$$Tse = Ts(\tau + \partial\tau, t + \partial t) - Ts(\tau, t) \tag{19}$$

$$Tse = Tmax \times (e^{+t/\tau} - e^{-(t + \partial t)/(\tau + \partial t)}) \tag{20}$$

In connection with the TRA formula, each of the terms A, B, C', and D is actually the difference between either T1 or T2 and the original ambient temperature Ta. Therefore, the net cumulative uncertainty for each of these terms can be expressed as a function of the uncertainties of the second measured temperature Tm (Either T1 or T2) and the original ambient temperature Ta:

$$\partial A = \partial B = \partial C' = \partial D = \partial Tm + \partial Ta \tag{21}$$

However, $$\partial Tm = \partial Ta = Tr + Tse \tag{22}$$

Therefore, $$\partial A = \partial B = \partial C' = \partial D = 2 \times Tr + 2 \times Tse \tag{23}$$

This is due to the fact that error terms always add, even when the normal (non-error) terms are subtracted. The net effect of adding error terms is to approximate a normal distribution function, with an average of zero and $+/-3\sigma$ points equal to $+/-$ the sum of all the error terms. In terms of imaging, this produces an image where, on average, the features are preserved but the speckle content is exaggerated.

From this, the uncertainty of the calculated image approximately can be expressed as:

$$\partial F = \partial C' + \partial D \times \frac{A +/- \partial A + \epsilon}{B +/- \partial B + \epsilon} \tag{24}$$

wherein the signs are chosen such that they maximize the $\partial D$ term. For all practical purposes, the uncertainty of $\epsilon$, can probably be ignored. In fact, the $\partial A$, $\partial B$ and $\epsilon$, terms can be ignored as long as $A >> \partial A$ and $B >> \partial B$. Two generalizations on the error in the derived defect-related image that describes those areas of the image where significant heating occurs versus those areas where little heating occurs can therefore be made.

Where the heating is significant, the error term approaches:

$$\partial F = \partial C + \partial D + \frac{A}{B} \quad (25)$$

$$= 2 + \frac{2 \times A}{B} \times (Tr + Tse)$$

Where the heating is minimal, the error term approaches:

$$\partial F = \partial C + \partial D \times \frac{\partial A + \epsilon}{\partial B + \epsilon} \quad (26)$$

But with minimal heating $\epsilon >> \partial A = \partial B$, so a good approximation is $$\partial F = \partial C + \partial D = 4 \times (Tr + Tse) \quad (27)$$

But, then again, with minimal heating $Tr >> Tse$, so this reduces to:

$$\partial F = 4 \times Tr \quad (28)$$

It should be obvious that noise in the TRA image can be reduced by minimizing Tr and Tse. Tr can be reduced significantly by interpolating (averaging) the values of the pixels of the TRA image with their nearest neighbors. This lessens the effect of quantizing the image. Likewise, Tse can be minimized by properly controlling the accuracy of the timing interval and making the timing interval as long as feasibly possible. From the formula for Tse, it can be seen that the effect of $\partial t$ and $\partial \tau$, can be minimized by making $t > 3\tau$ which allows the temperature to achieve greater than 95% of its steady state value. It was found that recording a thermogram four minutes after a step function thermal stimulus was first applied produced adequate results.

The flow diagram of the method of the invention shown in FIGS. 1-5 has been developed using commercially available thermal imagers such as the MIKRON® 6T62 Thermo Tracer. Such imagers rely upon an electro-mechanical scanning system to route received infrared radiation to a fixed discrete infrared sensor and it produces a raster image of thermal data which can be viewed by a standard video monitor or by means of a computer interface and monitor.

For testing integrated circuits mounted on boards, the technique could be modified to us a robotically controlled sensor to obtain data only at component (e.g., resistor, active device, or even an entire "chip") locations. This latter feature is desirable because it simplifies defect recognition data processing when used as an automated system.

In the flow diagram of FIG. 1, three two-dimensional arrays or image-like matrices of data points, that is, three thermal images, are acquired for a reference sample, in step 11. The first image is for the reference sample at stable ambient temperature.

It has been found that blowing compressed air at or just below ambient temperature over the sample will allow it to stabilize at ambient temperature relatively quickly. The second image is for the reference sample at a first elevated temperature, or in response to a first stimulus, which is, for example, a first voltage producing a first amount of heating in the sample. A second, typically more intense, stimulus is then applied to the reference sample to obtain a third image (which is the second image at elevated temperature). It has been found that a stimulus producing 5-10% more heating of the sample than the first stimulus is suitable. For each of the two different step-function stimuli, it was found that equal application times (e.g., for four minutes) produced substantially complete heating and was advantageous. Regardless of whether the two stimuli application times are equal, the application times for like-value stimuli must be the same as between the test and reference sample. Step 11 can be repeated for at least a second reference sample, unless one has some highly standardized previously tested samples of known good quality.

Figure 2:
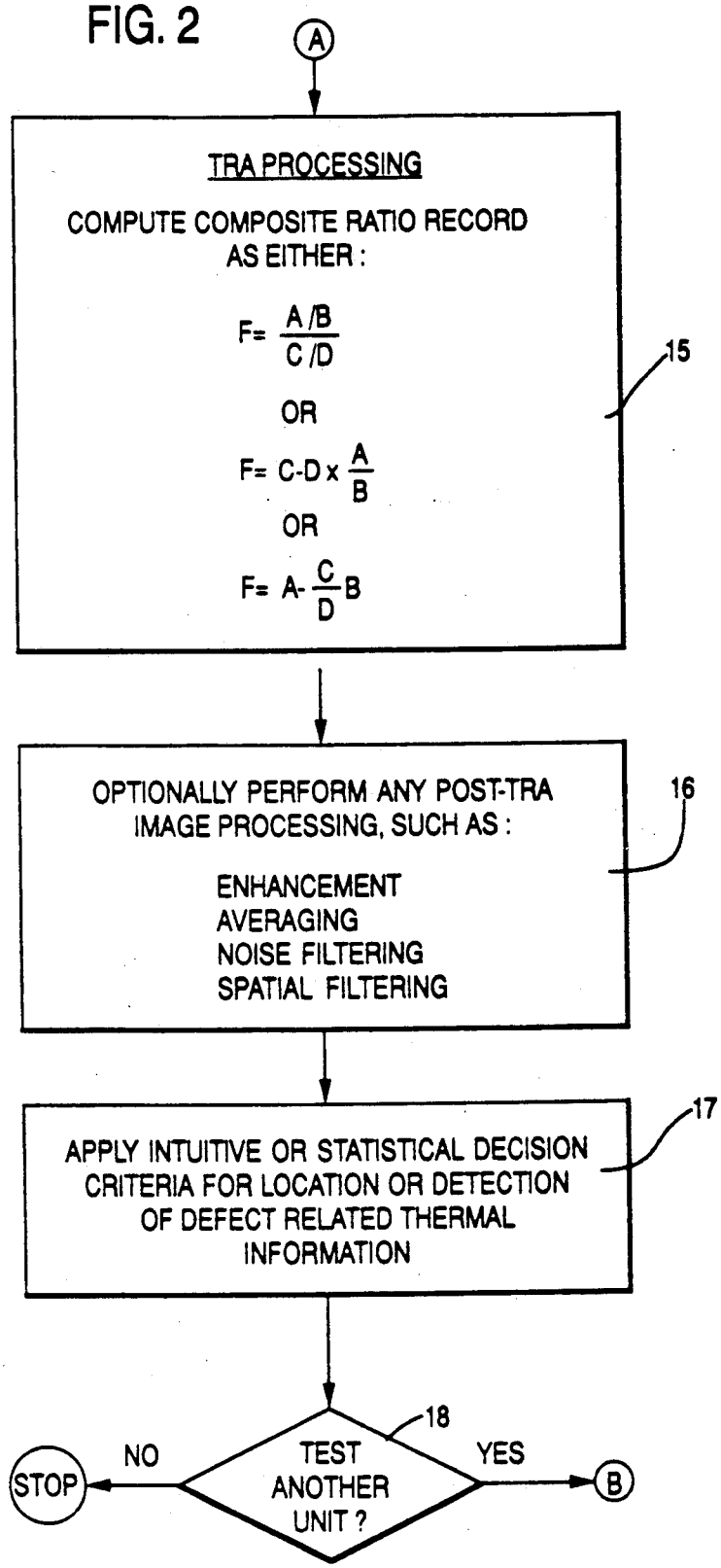

In step 12, the initial analysis steps characteristic of TRA are performed upon the sets of reference data, for each reference sample, the acquisition of which data was just described. Step 12 makes a first difference record B from the ambient temperature thermograph and one of the elevated temperature thermographs, and a second difference record D from the elevated temperature thermographs. In step 13, procedures as in steps 11 and 12 are repeated for the test sample replacing the reference sample. Before any ratios are taken, preliminary image processing steps are performed as indicated in step 14, if desired, as discussed below. As shown in FIG. 2, ratio analysis is then performed as shown in step 15, according to any one of the alternate formulas. In the first formula, "B" and "C" can be interchanged because division is commutative. Each ratio of step 15 for all the data points in each of two of the four difference records corresponds to a point in the sample. Since the TRA has proved to be a superior "normalizing" technique for thermography, it is feasible to do a quick "sanity" check in step 15, for example, by comparing ratio images for supposedly very similar "reference samples". Any markedly dissimilar results of the comparison will point to a failure to follow the proper testing technique, or failure to have obtained suitable reference test units.

Proper testing technique may require the following:

No air drafts except perhaps controlled air flow to maintain ambient temperature.

No heat sources near by (including the sample's own power supply).

Blow off with air jet to stabilize thermally. handling.

Pre-test staging location should TRA fixture to provide natural thermal equalization to actual test ambient conditions. This reduces the stabilization time achieved by means of the air jet.

Tape critical reflective points (being careful to prevent electrostatic defect generation upon later removal of the tape). It should be remembered the technique depends upon infrared radiation from the sample, and reflections are not desired. It is not required to so treat component leads.

Edge connectors typically used with semiconductor circuits should be thermally maintained at ambient to counteract warming from sample.

Avoid areas that experience large thermal shifts from air conditioning or sun-lit windows.

Block reflections from surrounding surfaces and bodies using baffles of low thermal mass and high emissivity.

Seek viewing angle that prevents the imager or detector from seeing itself in reflections from module. (This goal implies longer viewing distance and a small tilt of the sample relative to the sensor).

In some instances, would-be reference samples thought to be normal or non-defective are found not to be, and must be replaced.

Notice that the first formula, the fundamental formula, involves two ratios derived from the difference records in an ordered way, as may be seen by reference to FIG. 12, which ratio records are then further respectively subjected to the taking of ratios, point by point. The composite record then at each point comprises a ratio of ratios.

The first direct indication of deviation between the reference sample and the test sample can be obtained from the composite record of step 15, according to step 17. In many cases no further testing is necessary; and the procedures of step 16 may be skipped. An immediate decision can be made as to whether the test sample is sufficiently similar to the reference sample. In fact, step 17 can be performed automatically, by testing whether the composite record is featureless in respect of having no variations from the background which exceed a statistical limit such as a multiple of the standard deviation. The indication is then that there is no defect.

If an undesirable level of ambiguity persists after step 15 is performed, i.e., if a suspected defect produces differences from an image for the reference sample which do not exceed a first predetermined level ("three-sigma" level), but are still above a second, lower, predetermined level ("sigma" level), various image enhancement techniques can be employed, particularly with respect to the thermal ratio image for the test sample. In such techniques, the thermal ratio data is organized in the same two-dimensional way as in the original thermograph and, for example, can be viewed on the computer monitor. These are the optional post-ratio-analysis image processing steps shown in step 16.

Figure 4:
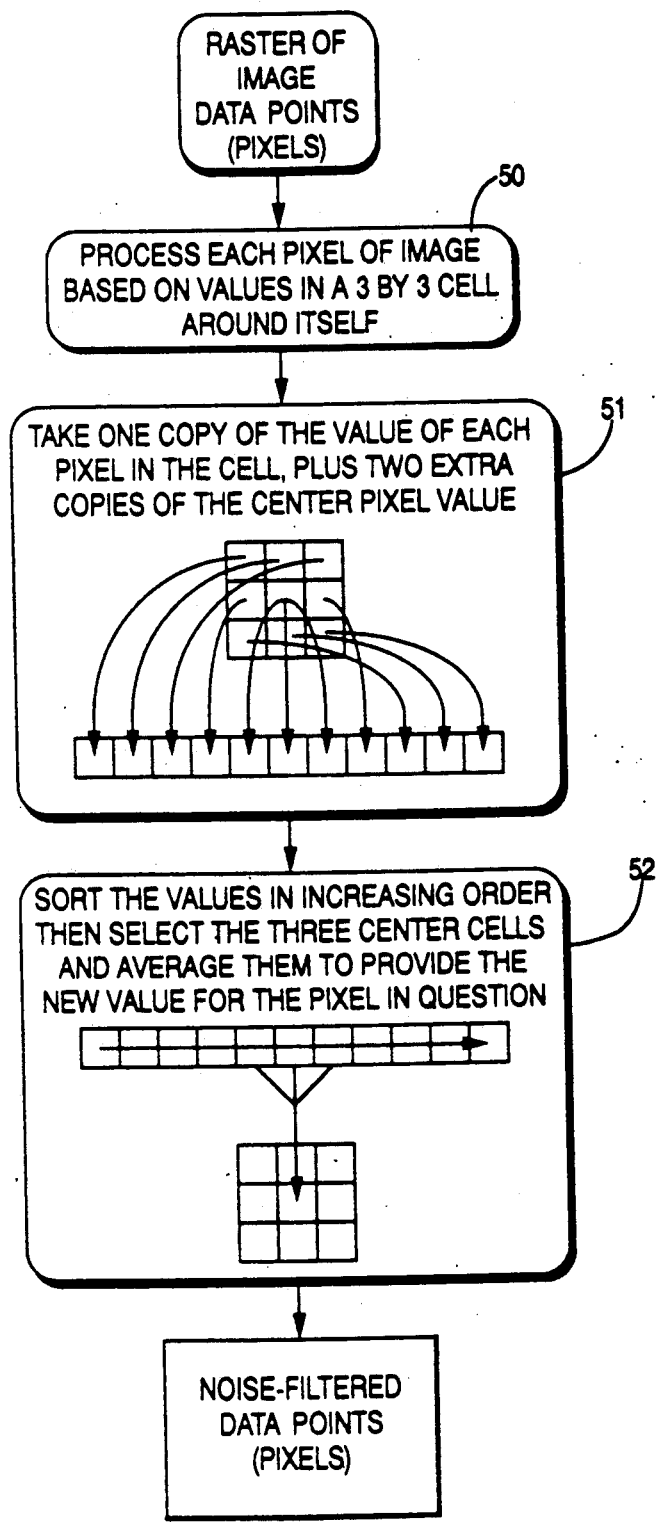

For example, in step 16, or as shown in FIG. 4, optional noise filtering is done. If the results are insufficient to reduce the level of ambiguity to make a decision possible, step 20 then removes by masking techniques any known non-defect-type artifacts found in either of both of the reference sample and the test sample. This a is specific example of techniques which are known in astronomy and reconnaissance photography as image enhancement techniques.

For further examples of possibly relevant enhancement techniques, see *Digital Image Processing*, by R. Gonzalez et al., Addison-Wesley (1987), pp. 162-163 (median filtering, pertaining to noise filtering); pp. 158-160 (local enhancement, pertaining to mask generation from original image data). As duly enhanced, the thermal ratio images are re-compared in step 17; and a decision is made as to the test sample, e.g., whether the first predetermined level or amount ("three-sigma" level) is exceeded at any point. The test apparatus and technique are ready to be applied to the next test samples, e.g., those coming down an assembly line for semiconductive integrated circuits, as indicated generally at step 18.

Figure 3:
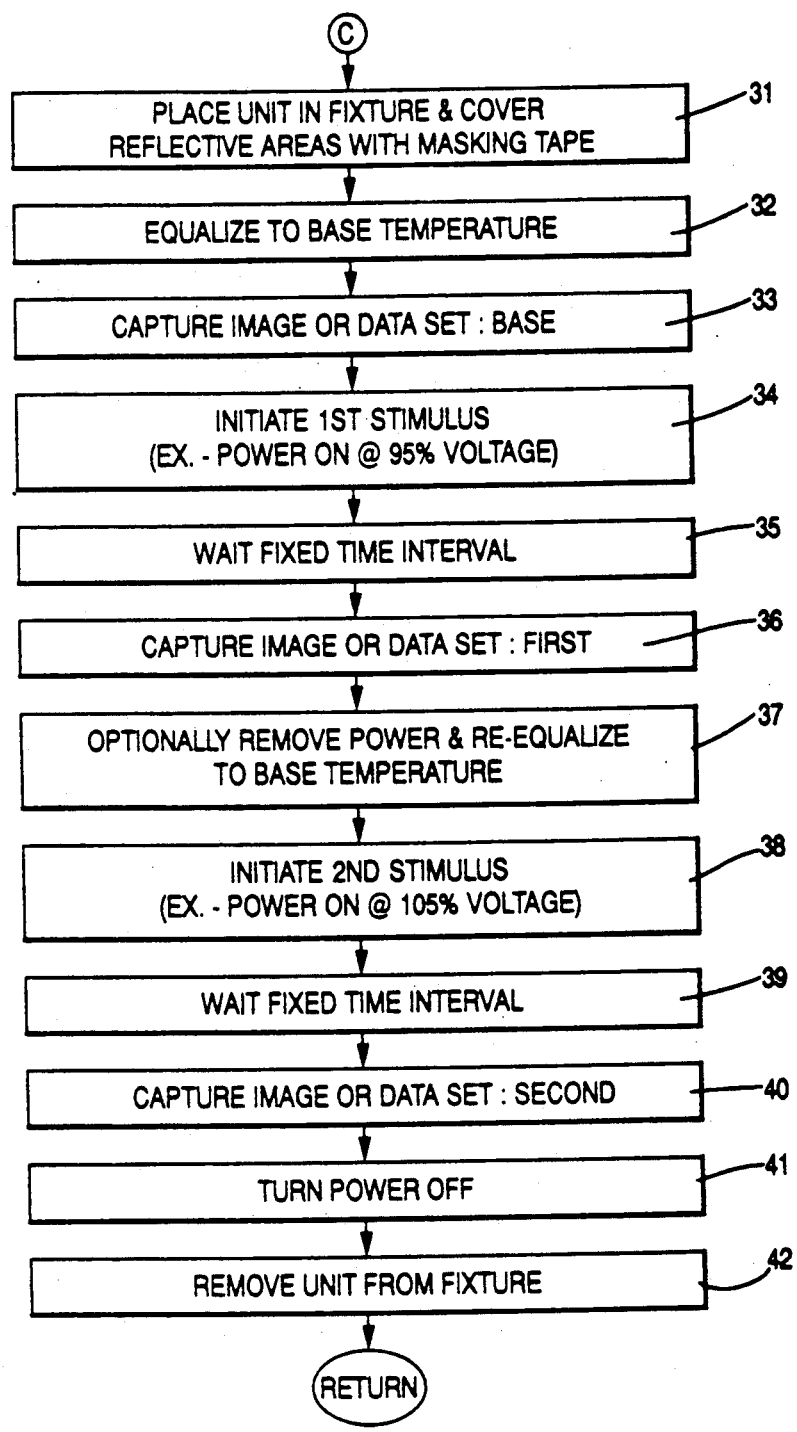

FIG. 3 shows the detailed steps in a portion of the procedure of FIGS. 1 and 2, as applied to a current-consuming product, and illustrates specific implementation of some of the points of good testing practice listed above. Of particular note in the detailed steps of FIG. 3, which are partially repetitive of those of FIGS. 1 and 2 is that the first and second elevated-temperature thermographs can be produced, in the case of the typical electronic component, by the application of voltages, close to normal operating voltages, which can be used for operating performance tests. For example, the successive thermal stimuli might be provided by 95% of normal operating voltage and 105% of normal operating voltage, as illustrated by steps 34, 36, 38 and 440 This versatility of the method is greatly facilitated by its wide dynamic range, which also signifies that these are not critical values of stimuli.

FIG. 4 consists of diagrams that deal with certain aspects of image enhancement, particularly noise filtering. Steps 50-52 relate to a relative smoothing between adjacent pixels of each thermal ratio image and for the resulting comparative image that will tend to filter speckle noise.

Figure 5:
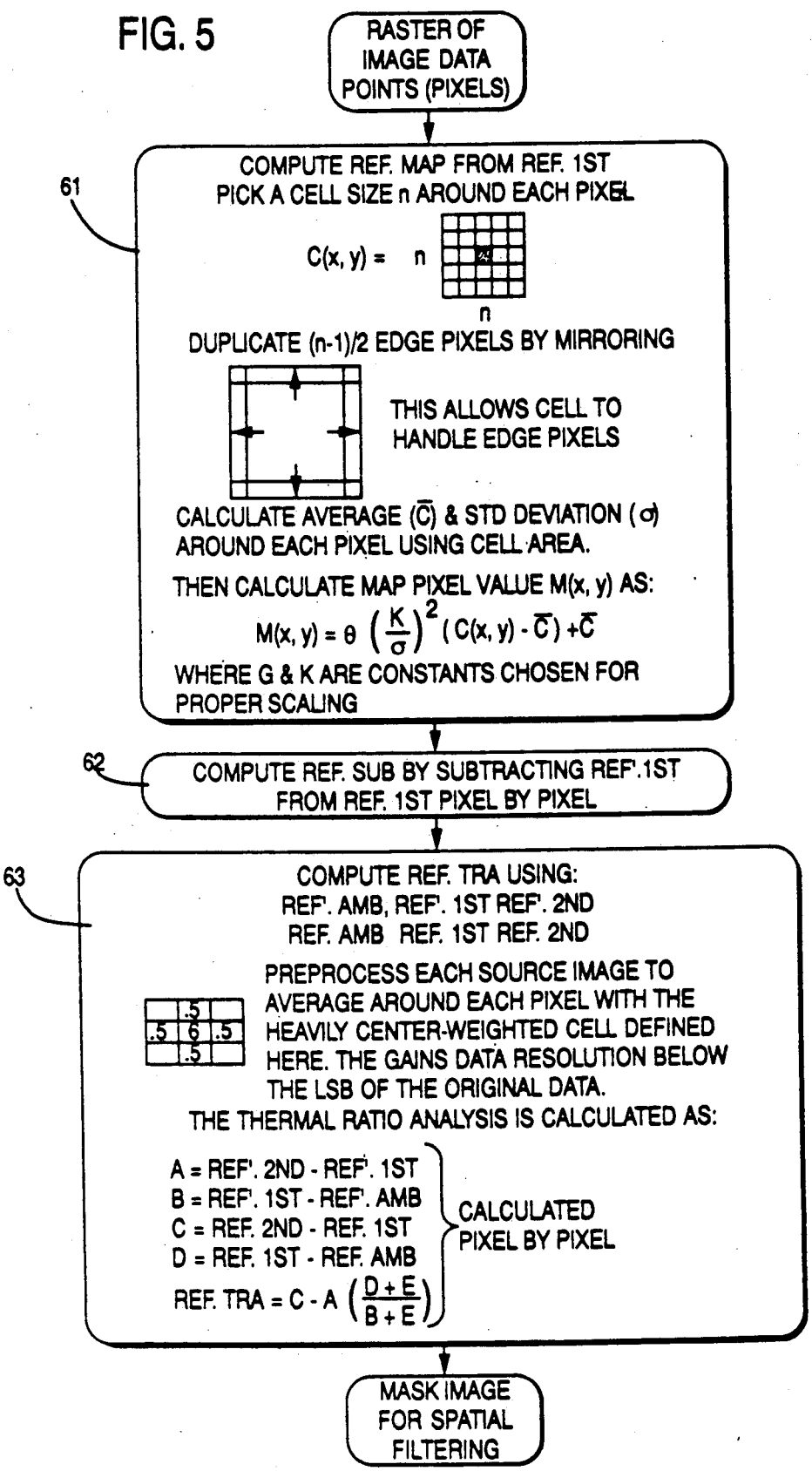

FIG. 5 shows yet another aspect of image enhancement that can be performed, per steps 61-63, with one or more of the original elevated temperature thermographs and is useful for generating one or more mask images for spatial filtering.

Figure 6:
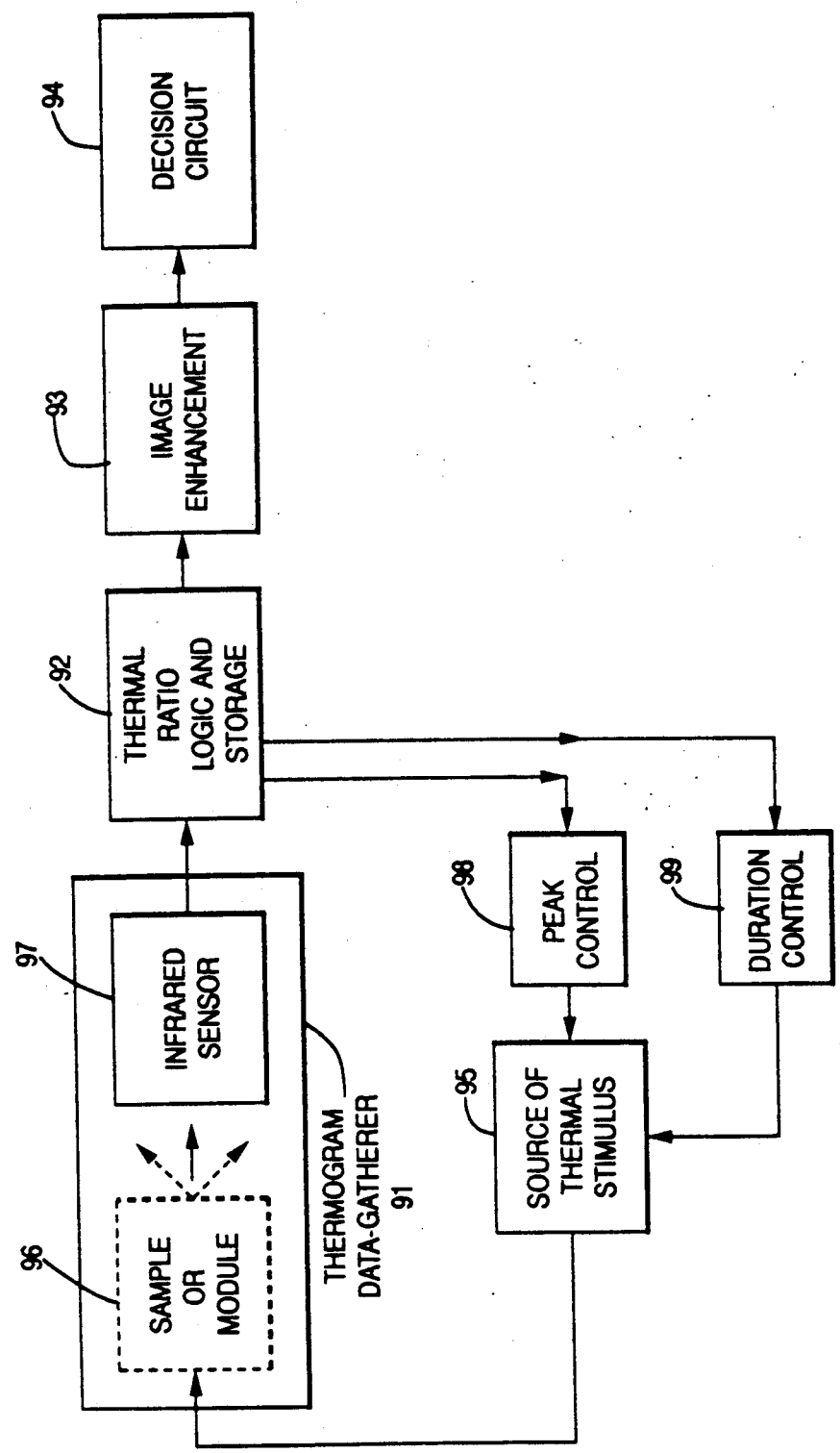
FIG. 6 is a diagram of a test set-up for practicing the method of the invention.

FIG. 6 shows the interrelationships among the items of equipment used in TRA.

The thermogram data-gatherer 91 is configured to hold a sample 96 from which infrared data is to be acquired. The data is acquired by the infrared sensor 97, that has typically a single, fixed discrete sensing element, which effectively samples or scans the exposed portion of sample 96 via an interposed scanning apparatus in sensor 97. In the preferred embodiment, the infrared sensor 97 is a thermo-tracer, for example, a MIKRON 6T62 thermo-tracer.

Alternatively, sensor 97 could be a semiconductor chargecoupled-device camera, thereby avoiding the electro-mechanical scanner of the MIKRON 6T62 thermo-tracer. The sequencing of image-type data points is then obtained purely electronically, for example, as is typically provided for such a camera.

The thermal ratio logic and storage unit 92 is basically a central processing unit which in addition to performing the calculations indicated above, coordinates the functioning of the image enhancement means 93, the decision circuit 94, as well as the timing through duration control and size, through peak control 98, of thermal stimuli applied from stimulus source 95 to sample 96, and the scanning of the sensor 97. Thus, the logic and storage means 92 obtains the various difference records, as well as the reference sample ratio image and the test sample ratio image. Image enhancement means 93 can use any of the above-described filtering, smoothing and other image enhancement techniques, as well as any of those known in the prior art. Indeed, again as described above, as well as performing in the position shown, image enhancement can act directly on thermographs before entering logic and storage unit 92, as well as on difference records obtained therein. Thus, the arrangement of FIG. 6 is merely illustrative.

Decision circuit 94 accepts or rejects test samples as having no defect or a defect of sufficient magnitude based upon the statistical analysis of the composite record, which for example, may show one more pixels deviating from the surrounding background by one or more standard deviations.

It should be understood that TRA is more broadly applicable to products than just semiconductor circuits or even electronic assemblies. All manufactured products (non-living) can be caused to experience controlled temperature excursions. While use on an assembly line may be a preferred use, it can also be used at any time in the life of a product, provided data, even archived data, from a reference sample of the product is available.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. A method of detecting defects in a test sample of a product, comprising the steps of:
   generating a reference record for at least one reference sample of the product that does not have defects, comprising the sub-steps of:
   (1) making an ambient-temperature thermal record of the reference sample at ambient temperature;
   (2) making a plurality of elevated temperature thermal records of the reference sample at a plurality of respective elevated temperatures, including applying a respective thermal stimulus to the reference sample, and
   (3) making a first difference record for the reference sample from the ambient-temperature thermal records and one of the plurality of elevated temperature thermal records and at least a second difference record for the reference sample involving at least another of the plurality of elevated temperature thermal records,
   generating first and at least second difference records for the test sample by repeating sub-steps (1)-(3) with the test sample replacing the reference sample;
   deriving at least one ratio record from the difference records for the reference sample and the test sample;
   forming a composite record including at least the derived one ratio record; and
   generating a defect indication when the composite record yields a statistical significant deviation from an expected value.

2. The method of detecting a defect according to claim 1, in which the sub-steps of making a plurality of elevated temperature thermal records include employing computerized control of the temperature.

3. The method of detecting a defect according to claim 1, in which the sub-steps of making a plurality of elevated temperature thermal records include allowing the passage of a fixed interval of time while each stimulus is applied.

4. The method of detecting a defect according to claim 1, in which the sub-step of making an ambient-temperature thermal record comprises stabilizing the thermal state of the sample by rapidly flowing gas from a compressed gas source around the sample at an effective temperature substantially equal to ambient temperature.

5. The method of detecting a defect according to claim 1, in which the sub-step of applying a respective thermal stimulus to the sample comprises employing the stimulus for a respective period of time different from a period of time for another respective thermal stimulus.

6. The method of detecting a defect according to claim 5, in which the sub-steps of making a plurality of elevated temperature thermal records include employing computerized control of each respective period of time.

7. The method of detecting a defect according to claim 5, in which the sub-steps of making a plurality of elevated temperature thermal records include allowing some temperature stabilization after an elevated temperature is reached.

8. The method of detecting a defect according to claim 4, in which the sub-step of stabilizing a sample at ambient temperature comprises rapidly flowing gas from a compressed gas source around it at an effective temperature substantially equal to ambient temperature.

9. A method of detecting a defect in a test sample of a product, comprising the steps of:
   establishing a reference record for at least one reference sample of the product that does not have defects, comprising the sub-steps of:
   (1) making a base thermal record of the reference sample at a base value of a thermal stimulus;
   (2) making a plurality of changed value thermal records of the reference sample at a plurality of respective changed values of the thermal stimulus, including applying a respective changed-value thermal stimulus to the reference sample; and
   (3) making a first difference record for the reference sample from the base-value thermal record and one of the plurality of elevated value thermal records and a second difference record for the reference sample involving at least another of the plurality of elevated value thermal records;
   generating first and second difference records for the test sample by repeating sub-steps (1)-(3) with test sample replacing the reference sample;
   deriving at least one ratio record from the four difference records consisting of the first and second difference records for the reference sample and the first and second difference records for the test sample;
   generating a defect indication when the composite ratio record yields a statistically significant deviation from an expected value.

10. The method of detecting a defect according to claim 9, in which the sub-step of making a plurality of changed value thermal records include employing computerized control of the value of the stimulus.

11. The method of detecting a defect according to claim 9, in which the sub-step of making a plurality of changed value thermal records include allowing some stabilization period after the stimulus is first applied.

12. The method of detecting a defect according to claim 9, in which the sub-step of making a base thermal record comprises stabilizing the sample by rapidly flowing gas from a compressed gas source around the sample at an effective temperature substantially equal to ambient temperature.

13. A method of detecting a defect in a test sample of a product, comprising the steps of:
   establishing a reference record for at least one reference sample of the product that does not have defects, comprising the sub-steps of:
   (1) making an ambient-temperature thermal record of the reference sample at ambient temperature,
   (2) making a plurality of elevated temperature thermal records of the reference sample at a plurality of respective voltages applied to the sample to produce heating therein, including applying a respective voltage to the reference sample;
   (3) making a first difference record from the ambient-temperature thermal records and one of the plurality of elevated temperature thermal records and a second difference record involving at least another of the plurality of elevated temperature;

generating a test record for the test sample by repeating sub-steps (1)–(3) with the test sample replacing the reference sample;

(4) deriving at least one ratio record from the four difference records consisting of the first and second difference records for the test sample and the first and second difference records for the reference sample;

forming a composite record including the at least one ratio record; and generating a defect indication when the composite record yields a statistically significant deviation from an expected value.

14. The method of detecting a defect according to claim 13, in which the sub-steps of making a plurality of elevated temperature thermal records include employing computerized control of the voltage.

15. The method of detecting a defect according to claim 13, in which the sub-steps of making a plurality of elevated temperature thermal records include allowing a period temperature stabilization after a respective voltage is first applied.

16. The method of detecting a defect according to claim 13, in which the sub-step of making an ambient-temperature thermal record comprises stabilizing the sample at ambient temperature by rapidly flowing gas from a compressed gas source around it at an effective temperature substantially equal to ambient temperature.

17. A system for thermally detecting a defect in a test sample of a product, comprising means for recording infrared data of a reference sample that does not have defects at ambient and elevated temperatures and for recording infrared data of the test sample at ambient and elevated temperatures;

means for forming a reference sample difference record from the infrared data of the reference sample at the ambient and elevated temperatures, and for forming a test sample difference record from the infrared data of the test sample at the ambient and elevated temperatures;

means for deriving at least one ratio from two of four difference records comprising said reference sample and test sample difference records;

means for converting the ratio into a composite record involving all the difference records; and means for generating a defect indication when the composite record yields a statistically significant deviation from an expected value.

18. The system of claim 17, further comprising means for enhancing the ratio record to remove potentially false defect indications.

19. The system of claim 18 further comprising means for removing speckle noise from the ratio record.

20. The system of claim 19 further comprising means for preprocessing the thermal records, or the difference records, prior to deriving the ratio record.

21. A method of detecting defects in a test sample of a product, comprising the steps of:

generating a reference record for at least one reference sample of the product that does not have defects, comprising the sub-steps of:

(1) making an ambient-temperature thermograph of the reference sample at ambient temperature;

(2) making a plurality of elevated temperature thermographs of the reference sample at a plurality of respective elevated temperatures, including applying a respective thermal stimulus to the reference sample, and (3) making a first difference record for the reference sample from the ambient-temperature thermograph and one of the plurality of elevated temperature thermographs and a second difference record for the reference sample involving at least another of the plurality of elevated temperature thermographs, the first and second difference records each comprising a plurality of image-type data points in an image-related array, generating first and second difference records for the test sample by repeating sub-steps (1)–(3) with the test sample replacing the reference sample;

deriving at least one second ratio record from the four difference records consisting of the first and second difference records for the reference sample and the first and second difference records for the test sample, the ratio record including data points corresponding to respective data points in at least one of the difference records;

generating a defect indication when the composite record has at least one discrete region of substantially greater than average contrast with respect to surrounding regions.

22. The method of detecting a defect according to claim 21, in which the sub-steps of making a plurality of elevated temperature thermographs include employing computerized control of the thermal stimulus.

23. The method of detecting a defect according to claim 21, in which the sub-steps of making a plurality of elevated temperature thermographs include allowing the passage of a fixed interval of time while each stimulus is applied.

24. The method of detecting a defect according to claim 21, in which the sub-step of making an ambient-temperature thermograph comprises stabilizing the thermal state of the sample by rapidly flowing gas from a compressed gas source around the sample at an effective temperature substantially equal to ambient temperature.

25. The method of detecting a defect according to claim 21, in which the sub-step of applying a respective thermal stimulus to the sample comprises employing the stimulus for a respective period of time difference from a period of time for another respective thermal stimulus.

26. The method of detecting a defect according to claim 25, in which the sub-steps of making a plurality of elevated temperature thermographs include employing computerized control of each respective period of time.

27. The method of detecting a defect according to claim 25, in which the sub-steps of making a plurality of elevated temperature thermographs include allowing some temperature stabilization after an elevated temperature is reached.

28. The method of detecting a defect according to claim 24, in which the sub-step of stabilizing a sample at ambient temperature comprises rapidly flowing gas from a compressed gas source around it at an effective temperature substantially equal to ambient temperature.

29. A method of detecting a defect in a test sample of a product, comprising the steps of:

establishing a reference record for at least one reference sample of the product that does not have defects, comprising the sub-steps of:

(1) making a base thermograph of the reference sample at a base value of a thermal stimulus;

(2) making a plurality of changed value thermographs of the reference sample at a plurality of respective changed values of the thermal stimulus, including applying a respective changed-value thermal stimulus to the reference sample; and (3) making a first difference record for the reference sample from the base-value thermograph and one of the plurality of elevated value thermographs and a second difference record for the reference sample involving at least another of the plurality of elevated value thermographs, the first and second difference records each comprising a plurality of image-type data points in an image-related array;

generating first and second difference records for the test sample by repeating sub-steps (1)-(3) with the test sample replacing the reference sample;

deriving at least one ratio record from the four difference records consisting of the first and second difference records for the reference sample and the first and second difference records for the test sample, the ratio record including data points corresponding to the respective data points in at least one of the difference records;

forming a composite record including at least the one derived ratio record; and generating a defect indication when the composite record has at least one discrete region of substantially greater than average contrast with respect to surrounding regions.

30. The method of detecting a defect according to claim 29, in which the sub-step of making a plurality of changed value thermographs include employing computerized control of the value of the stimulus.

31. The method of detecting a defect according to claim 29, in which the sub-step of making a plurality of changed value thermographs include allowing some stabilization period after the stimulus is first applied.

32. The method of detecting a defect according to claim 29, in which the sub-step of making a base thermograph comprises stabilizing the sample by rapidly flowing gas from a compressed gas source around the sample at an effective temperature not exceeding ambient temperature.

33. A method of detecting a defect in a test sample of a product, comprising the steps of:
establishing a reference record for at least one reference sample of the product that does not have defects, comprising the sub-steps of:
(1) making an ambient-temperature thermograph of the reference sample at ambient temperature,
(2) making a plurality of elevated temperature thermographs of the reference sample at a plurality of respective voltages applied to the sample to produce heating therein, including applying a respective voltage to the reference sample;
(3) making a first difference record from the ambient-temperature thermographs and one of the plurality of elevated temperature thermographs and a second difference record involving at least another of the plurality of elevated temperature thermographs, the first and second difference records each comprising a plurality of image-type data points in an image-related array;

generating a test record for the test sample by repeating sub-steps (1)-(3) with the test sample replacing the reference sample;

(4) deriving at least one ratio record from the four difference records consisting of the first and second difference records for the test sample and the first and second difference records for the reference sample, the ratio record including data points corresponding to respective data points in at least one of the difference records;

forming a composite record including the at least one ratio record; and generating a defect indication when the composite record has at least one discrete region of substantially greater than average contrast with respect to surrounding regions.

34. The method of detecting a defect according to claim 33, in which the sub-steps of making a plurality of elevated temperature thermographs include employing computerized control of the voltage.

35. The method of detecting a defect according to claim 33, in which the sub-steps of making a plurality of elevated temperature thermographs include allowing a period temperature stabilization after a respective voltage is first applied.

36. The method of detecting a defect according to claim 33, in which the sub-step of making an ambient-temperature thermograph comprises stabilizing the sample at ambient temperature by rapidly flowing gas from a compressed gas source around it at an effective temperature not exceeding ambient temperature.

37. A system for thermally detecting a defect in a test sample of a product, comprising
means for forming infrared images of a reference sample that does not have defects at ambient and elevated temperatures and for forming infrared images of the test sample at ambient and elevated temperatures, each of the images comprising a plurality of image data points;
means for forming reference sample difference records from the images of the reference sample at the ambient and elevated temperatures, and for forming test sample difference records from the images of the test sample at the ambient and elevated temperatures;
means for forming at least one ratio record from two of four difference records comprising said reference sample difference records and test sample difference records;
means for converting the ratio record into a composite record involving all the difference records; and
means for generating a defect indication when the composite record has at least one discrete region of substantially greater than average contrast with respect to surrounding regions.

38. The system of claim 37, further comprising means for enhancing the ratio record to remove potentially false defect indications.

39. The system of claim 38 further comprising means for removing speckle noise from the ratio record.

40. The system of claim 38 further comprising means for preprocessing the thermographs, or the difference records, prior to deriving the ratio record.

* * * * *